(12) United States Patent
Coffed et al.

(10) Patent No.: US 7,630,768 B1
(45) Date of Patent: Dec. 8, 2009

(54) ONE-PIECE HEADER ASSEMBLY FOR AN IMPLANTABLE MEDICAL DEVICE AND METHODS FOR MAKING SAME

(75) Inventors: James Coffed, Depew, NY (US); James Kinney, Clarence, NY (US); James C. Biggs, Jr., East Aurora, NY (US); Joseph Gray, Eden, NY (US)

(73) Assignee: Greatbatch Ltd., Clarence, NY (US)

( * ) Notice: Subject to any disclaimer, the term of this patent is extended or adjusted under 35 U.S.C. 154(b) by 281 days.

(21) Appl. No.: 11/538,455

(22) Filed: Oct. 4, 2006

(51) Int. Cl.
*A61N 1/00* (2006.01)
(52) U.S. Cl. ...................................... 607/37
(58) Field of Classification Search .................. 607/37, 607/36
See application file for complete search history.

(56) References Cited

U.S. PATENT DOCUMENTS

| | | | |
|---|---|---|---|
| 4,212,510 A | 7/1980 | Ritchie et al. | |
| 4,296,390 A | 10/1981 | Vanderheyden et al. | |
| 5,336,246 A * | 8/1994 | Dantanarayana | 607/37 |
| 5,844,198 A * | 12/1998 | Jones et al. | 219/121.64 |
| 6,975,906 B2 * | 12/2005 | Rusin et al. | 607/36 |
| 7,069,081 B2 | 6/2006 | Biggs et al. | |
| 7,187,535 B1 * | 3/2007 | Iyer et al. | 361/302 |
| 7,239,916 B2 * | 7/2007 | Thompson et al. | 607/30 |
| 7,260,434 B1 * | 8/2007 | Lim et al. | 607/37 |
| 7,396,265 B2 * | 7/2008 | Darley et al. | 439/885 |
| 2002/0107555 A1 * | 8/2002 | Rusin et al. | 607/37 |
| 2002/0138114 A1 * | 9/2002 | Gramse | 607/37 |
| 2003/0163171 A1 | 8/2003 | Kast et al. | |
| 2004/0122481 A1 | 6/2004 | Tidemand et al. | |
| 2005/0033371 A1 | 2/2005 | Sommer et al. | |
| 2005/0131481 A1 | 6/2005 | Ries et al. | |
| 2005/0131483 A1 | 6/2005 | Zhao et al. | |
| 2005/0149140 A1 | 7/2005 | Hansen et al. | |
| 2006/0015150 A1 * | 1/2006 | Rusin et al. | 607/36 |
| 2006/0047321 A1 * | 3/2006 | Biggs et al. | 607/37 |
| 2007/0179553 A1 * | 8/2007 | Iyer et al. | 607/37 |

\* cited by examiner

*Primary Examiner*—George Manuel
(74) *Attorney, Agent, or Firm*—Michael F. Scalise

(57) ABSTRACT

A header assembly for connecting an implantable medical device to at least one conductor lead terminating within a patient intended to be assisted by the medical device is provided. The implantable medical device is comprised of at least one feedthrough wire extending from the control circuitry and through a wall of the housing. The header assembly is comprised of an insulative body that is mountable on the housing of the medical device. The insulative body supports at least one conductor subassembly comprising a terminal that is directly connectable to the conductor lead, an intermediate conductor comprising a distal end connected to the terminal and a proximal end connected to a connector. Methods for making the header assembly and for connecting the header assembly to the implantable medical device are also disclosed.

25 Claims, 11 Drawing Sheets

ONE-PIECE HEADER ASSEMBLY FOR AN IMPLANTABLE MEDICAL DEVICE AND METHODS FOR MAKING SAME

BACKGROUND OF THE INVENTION

1. Field of the Invention

The invention relates to a one-piece molded polymeric header assembly for connecting an implantable medical device to a body organ assisted by the medical device. More particularly, the present invention relates in one embodiment to methods for making a one-piece header assembly in which the embedded electrical connectors are precisely located within the molded polymeric header body.

2. Description of Related Art

Implantable medical devices have feedthrough conductors in the form of pins or wires connected to the internal components of the medical device. The feedthrough wires extend through a wall of the medical device housing and are electrically insulated there from by a ceramic-to-metal seal or a glass-to-metal seal. Electrical continuity to a conductor lead attached to the body being assisted is established by connecting intermediate conductor wires supported by a polymeric header mounted on the medical device to the feedthrough wires of the implantable device and terminal blocks in the molded header body. The terminal blocks then provide for plugging the conductor lead into the molded polymeric header. Examples of this type of header assembly are shown in U.S. Pat. No. 4,254,775 to Langer, U.S. Pat. No. 4,262,673 to Kinney et al., U.S. Pat. No. 4,764,132 to Stutz, Jr., U.S. Pat. No. 5,282,841 to Szyszkowski and U.S. Pat. No. 5,336,246 to Dantanarayana. The disclosures of these U.S. patents are incorporated herein by reference.

U.S. Patent Application Pub. No. 2004/0093038 of Biggs et al., which is assigned to the assignee of the present invention and incorporated herein by reference, discloses a header assembly comprising a body of polymeric material supporting at least one unitary conductor wire. The header may have multiple conductor wires. The conductor wires connect between feedthrough wires exiting the medical device and terminal blocks into which conductor leads plug.

Implantable medical devices have become more complex in recent years. In addition to providing a stimulus or other beneficial treatment to a body organ, the devices may include sensors and/or remote imaging devices which are to be connected to the circuitry within the device casing. The devices may also perform more than one medical function. Due to the growing complexity of implantable medical devices, there is a need for a header that provides a greater number of electrical connectors for leads and sensors that are connected to the device. The size of the header must be maintained approximately constant, with the electrical connectors closely spaced therein. There is thus a need for a molded polymeric header in which the electrical wires and terminal blocks are located with a high degree of precision. This is so a reliable electrical connection can be made with all of the associated feedthrough wires exiting the medical device. There is also a need for a method to connect a medical device having a complex array of feedthrough wires to a header with a correspondingly complex array of electrical conductors.

SUMMARY OF THE INVENTION

Accordingly, embodiments of the present invention are provided that meet at least one or more of the following objects.

It is an object of this invention to provide a molded polymeric header assembly for an implantable device wherein the assembly has a high density of electrical connectors precisely located and embedded therein.

It is a further object of this invention to provide tools, apparatus, and methods for making a molded polymeric header assembly with a high density of electrical connectors precisely located and embedded therein, and for connecting such a header assembly to an implantable medical device.

According to the present invention, therefore, a header assembly for connecting an implantable medical device to at least one conductor lead terminating within a patient intended to be assisted by the medical device is provided. The implantable medical device is comprised of a housing containing control circuitry, at least one electrical energy storage device, and at least one feedthrough wire extending from the control circuitry and through a wall of the housing. The header assembly is comprised of an insulative body that is mountable at a bottom surface thereof on the housing of the medical device, and at least one conductor subassembly comprising a terminal supported by the insulative body, wherein the terminal is directly connectable to the at least one conductor lead; an intermediate conductor comprising a distal end connected to the terminal, and a proximal end; and a connector receptacle. The connector includes an outer surface, a distal end including a distal bore, a central region, a proximal end including a proximal bore, and a through hole extending from the outer surface into the proximal bore. The distal end of the connector is supported by the insulative body, the proximal end of the intermediate conductor is disposed within the distal bore of the connector, and the proximal bore of the connector is connectable to the at least one feedthrough wire of the implantable medical device. In the preferred embodiment, a connection inlet is provided in the bottom surface of the insulative body, and the proximal end of the connector including the proximal bore and the through hole therein are disposed within the gap. In this manner, the proximal end of the connector is exposed, and may be connected to the at least one feedthrough wire by a fusing operation, for example anyone of a number of welding techniques such as laser welding or resistance welding.

The implantable device may be comprised of a plurality of feedthrough wires extending from the control circuitry and through a wall of the housing. A corresponding header assembly further comprises an equal plurality of additional conductor subassemblies, the structures of which are as recited above. In one exemplary embodiment, the header assembly is comprised of eight conductor subassemblies, which may be arrayed in two groups of four subassemblies. In another embodiment, the insulative body of the header assembly is comprised of an extended boss supporting the distal end and the central region of each of the connectors of the conductor subassemblies.

The insulative body of the header assembly is preferably of a molded polymeric material. The terminal, the intermediate conductor, and the connector of the at least one conductor subassembly may consist essentially of titanium. The connector receptacle preferably has a cylindrical shape. The medical devices to which the instant header assembly may be fitted include, but are not limited to, a hearing assist device, a neurostimulator, a cardiac pacemaker, a drug pump, a cardiac defibrillator, and an obesity control device.

Also according to the present invention, there is provided a method for making a header assembly for connecting an implantable medical device to at least one conductor lead terminating within a patient intended to be assisted by the medical device. The method comprises the steps of providing at least one conductive connector receptacle comprising an outer surface, a distal end including a distal bore, a central region, and a proximal end including a proximal bore; providing a feedthrough adapter holder comprised of a plate shaped body including an upper surface, a lower surface, a side wall, and at least one through bore extending from the upper surface to the lower surface, the through hole having a diameter sized to enable a press fit of the conductive connector therein; fitting the conductive connector into the through bore such that the plate shaped body of the feedthrough adapter holder is engaged with the central section of the conductive connector; drilling a through hole in the conductive connector from the outer surface into the proximal bore thereof; moving the feedthrough adapter holder so that it is engaged with the distal end of the conductive connector including the through hole thereof; providing at least one conductor wire comprising a distal end and a proximal end, and inserting the proximal end of the conductor wire into the distal bore of the conductive connector, and joining them together; positioning the conductor wire in a fixture so that its distal end is joinable to a terminal; providing at least one terminal, and joining the terminal to the distal end of the conductor wire to form at least one conductor subassembly comprising the conductive connector, the conductor wire, and the terminal; placing the at least one conductor subassembly in a mold cavity; molding a monolithic polymeric header body around the at least one conductor subassembly to form the header assembly; removing the header assembly from the mold; and removing the feedthrough adapter holder from the distal end of the connector.

The step of placing the at least one conductor subassembly in a mold cavity may include engaging the terminal with a mold insert provided in the shape of a conductor lead connector, so as to form an opening in the polymeric header body for connecting a conductor lead to the terminal. This step may alternatively or additionally include placing a mold insert within the mold cavity, wherein the mold insert comprises a recessed cavity comprising a bottom surface and a side surface terminating at an upper surface. The feedthrough adapter holder is disposed in the recessed cavity such that the bottom surface of the recessed cavity is contiguous with the lower surface of the feedthrough adapter holder, and the side surface of the recessed cavity is continuous with the side wall of the feedthrough adapter holder. The upper surface of the feedthrough adapter holder may be located below the upper surface of the mold insert and within the recessed cavity, thereby forming a boss cavity. The resulting molded header body comprises an extended boss formed within the boss cavity. Additionally, the at least one through hole in the feedthrough adapter holder may have a counter bore, and the bottom surface of the recessed cavity in the mold insert may have at least one pedestal disposed in the counter bore of the through hole in the feedthrough adapter holder.

The header made according to the instant method may be comprised of a plurality of subassemblies similar to the one described above. The feedthrough adapter holder may consist essentially of polysulfone polymeric, or polyetheretherketone polymeric. The terminals, the intermediate conductors, and the connector of the conductor subassemblies may consist essentially of titanium or other suitable conductive materials.

The conductor wires of the conductor subassemblies may be pre-formed into the desired shapes to be supported within the polymeric header body prior to the step of positioning the conductor wires in the fixture. The step of drilling the through hole in the connector is preferably performed by electrical discharge machining or by laser machining. The step of joining the conductor wire to the conductive connector may be performed by press fitting the proximal end of the conductor wire into the distal bore of the connector, or by welding the proximal end of the conductor wire to the distal end of the connector.

Also according to the present invention, there is provided a method for connecting a header assembly to an implantable medical device, comprising the steps of providing the implantable medical device comprising a housing containing control circuitry, at least one electrical energy storage device, and at least one feedthrough wire extending from the control circuitry and through a wall of the housing, and providing the header assembly comprised of an insulative body that is mountable at a bottom surface thereof to the housing of the medical device, and at least one conductor subassembly. The conductor subassembly is comprised of a terminal supported by the insulative body, an intermediate conductor comprising a distal end connected to the terminal, and a proximal end, and a connector. The connector includes an outer surface, a distal end including a distal bore, a central region, a proximal end including a proximal bore, and a through hole extending from the outer surface into the proximal bore, wherein the distal end of the connector is supported by the insulative body, the proximal end of the intermediate conductor is disposed within the distal bore of the connector, and the proximal end of the connector including the through hole is exposed in a recess in the bottom surface of the insulative body.

The method further includes the steps of positioning the header assembly proximate to the implantable device wherein the at least one feedthrough wire is disposed in the proximal bore of the connector of the at least one conductor subassembly, and the bottom surface of the insulative body is proximate to the wall of the housing of the implantable medical device; and directing at least one laser beam through the through hole in the proximal bore of the connector onto the at least one feedthrough wire disposed therein, and laser welding the feedthrough wire to the connector of the conductor subassembly.

In one embodiment, the implantable device and the header assembly may be configured such that after performing the step of positioning the header assembly proximate to the implantable device, an interstice is present between at least a portion of the bottom surface of the insulative body proximate the wall of the housing of the implantable medical device. In this embodiment, the step of sealing the bottom surface of the insulative body to the wall of the housing of the implantable medical device may be performed by filling the interstice with a curable liquid sealant. The resulting cured liquid sealant may consist essentially of an organopolysiloxane.

For example, the implantable medical device to be connected to the header assembly according to the instant method may be comprised of eight feedthrough wires extending from the control circuitry and through the wall of the device housing. The header is correspondingly comprised of eight conductor subassemblies comprising eight conductive connectors correspondingly positioned to receive the eight feedthrough wires of the implantable medical device in the proximal bores thereof. The eight feedthrough wires may be positioned in a pattern of two sets of four wires. The eight connectors are positioned in a corresponding pattern of two sets of four connectors so that the eight feedthrough wires are disposable individually in the proximal bores of the eight connectors.

The implantable medical device and the header assembly each comprise a proximal side and a distal side. In a further embodiment, the through holes in the proximal bores of a first group of four wires are viewable from the proximal side of the header assembly, and the through holes in the proximal bores of a second group of four wires are viewable from the distal side of the header assembly. The laser beam is directed through the through holes in the proximal bores of the first group of four wires from the proximal side of the header assembly, and then through the through holes in the proximal bores of the second group of four wires from the distal side of the header assembly, thereby laser welding the eight feedthrough wires of the implantable medical device to the eight connectors of the header assembly.

The foregoing and additional objects, advantages, and characterizing features of the present invention will become increasingly more apparent upon a reading of the following detailed description together with the included drawings.

BRIEF DESCRIPTION OF THE DRAWINGS

The present invention will be described by reference to the following drawings, in which like numerals refer to like elements, and in which:

FIG. 8 is a cross-sectional view of the header assembly connected to an implantable device, including a seal provided there between;

Figure 1:
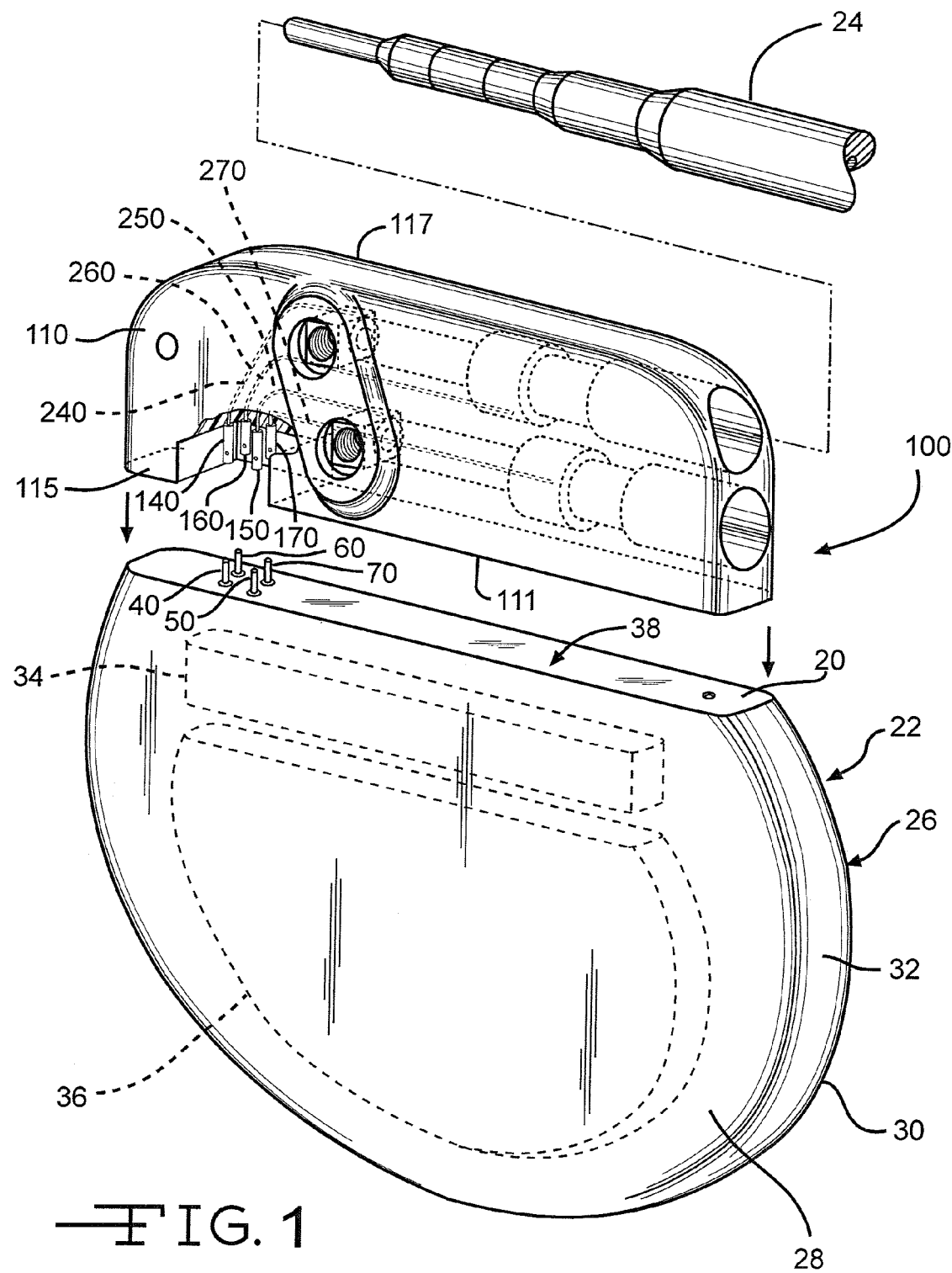
FIG. 1 is an exploded view of a header assembly mounted on an implantable medical device according to the present invention.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by the appended claims.

DETAILED DESCRIPTION OF THE PREFERRED EMBODIMENTS

For a general understanding of the present invention, reference is made to the drawings. In the drawings, like reference numerals have been used throughout to designate identical elements.

FIG. 1 is an exploded view of a header assembly mounted on an implantable medical device according to the present invention. Implantable medical device 22 comprises a housing 26 of a conductive material, such as of titanium or stainless steel. Preferably, the medical device housing 26 is comprised of mating clam shells in an overlapping or butt welded construction, as shown in U.S. Pat. No. 6,613,474 to Frustaci et al. This patent is assigned to the assignee of the present invention and incorporated herein by reference. The housing 26 can also be of a deep drawn, prismatic and cylindrical design, as is well known to those skilled in the art.

The housing 26 is shown in an exemplary form comprising first and second planar major face walls 28 and 30 joined together by a sidewall 32 and the header wall 20. The sidewall 32 curves from one end of the header wall 20 to the other end and is generally arcuate from face wall 28 to face wall 30. The preferred mating clam shells of housing 26 are hermetically sealed together, such as by laser or resistance welding, to provide an enclosure for the medical device including its control circuitry 34 and a power supply 36, such as a battery (the control circuitry and power supply are shown in dashed lines in FIG. 1). The power supply 36 is connected to the control circuitry 34 by electrical leads (not shown). There may also be a capacitor for a medical device such as a defibrillator. The implantable medical device 22 is exemplary of any one of a number of known assist devices such as cardiac defibrillators, cardiac pacemakers, drug pumps, neurostimulators, hearing assist devices, and the like.

Header wall 20 of housing 26 has a planar upper surface 38 providing at least one opening through which a feedthrough wire passes. In the embodiment depicted in FIG. 1, the upper surface 38 of housing 26 includes four openings through which respective feedthrough wires 40, 50, 60, and 70 pass. The feedthrough wires extend from a distal end positioned inside the housing 26 connected to the control circuitry 34 to respective proximal ends spaced above the housing upper surface 38. The feedthrough wires 40, 50, 60, and 70 are electrically insulated from the housing 26 by respective ceramic-to-metal seals or glass-to-metal seals (not shown), as are well known by those skilled in the art.

Header assembly 100 is comprised of an insulative body 110 that is mountable along bottom surface 111 on the housing 26 of the medical device 22, and at least one conductor subassembly comprising a terminal supported by the insulative body. The terminal is directly connectable to at least one conductor lead 24. The conductor assembly further comprises an intermediate conductor comprising a distal end connected to the terminal and a proximal end, and a connector receptacle. In the embodiment depicted in FIG. 1, header assembly 100 is comprised of four conductor subassemblies. A gap 113 (see FIG. 6) is provided in the bottom surface of the insulative body, and the proximal ends of the connectors including the proximal bore and the through holes therein are disposed within the gap, as will be described subsequently herein.

Much of the structure of header assembly 100 is similar to the header assembly 10 of the aforementioned U.S. Patent Application Pub. No. 2004/0093038 of Biggs et al. and will not be recited again in this disclosure. However, a major difference between the competing header assemblies is the manner in which the intermediate conductors are connected to the feedthrough wires of the implantable device, as will be explained presently. In the following disclosure, methods for making the header assemblies of the present invention and connecting them to implantable devices will be described. In providing the description of these methods, the structure of the header assemblies will also be described.

Figure 2:
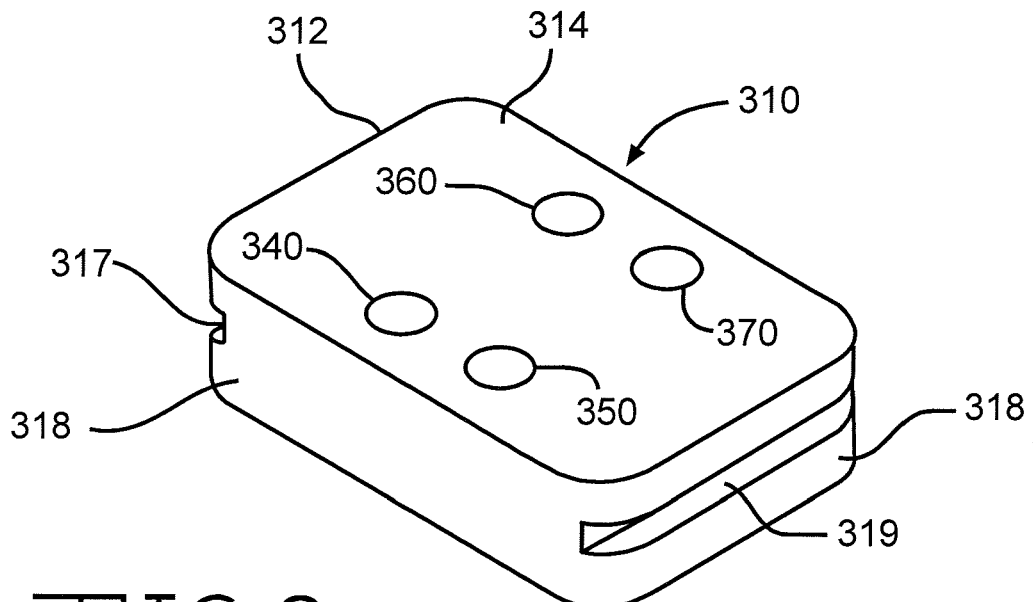
FIG. 2 is a perspective view of a feedthrough adapter holder used in making the header assembly of the present invention.
Figure 3:
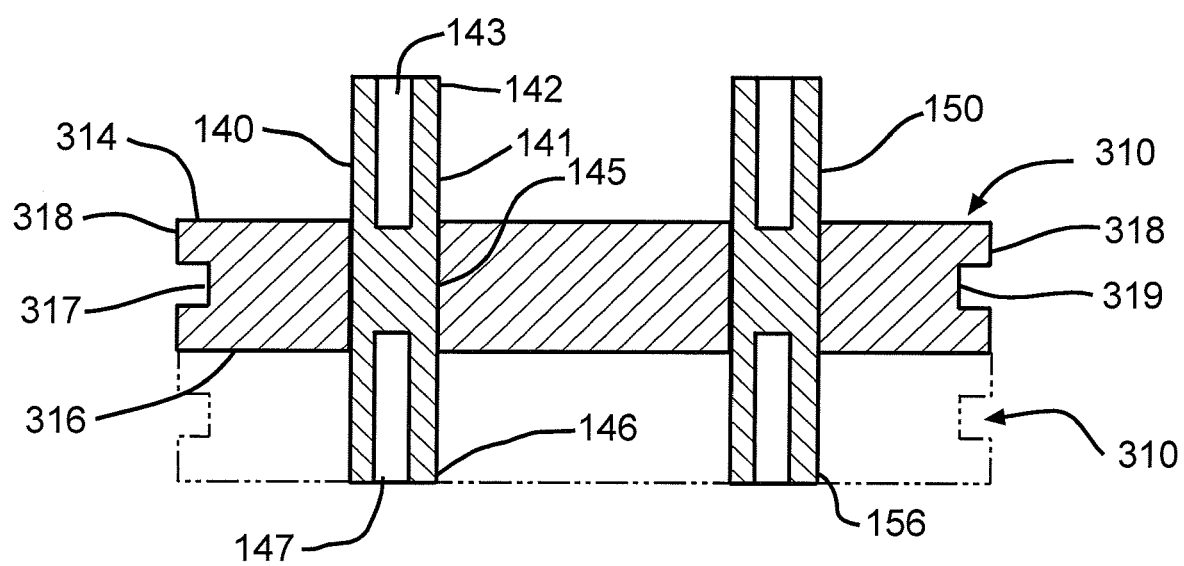
FIG. 3 is a cross-sectional view of the feedthrough adapter holder of FIG. 2, with conductive connectors of the header assembly press fitted within through holes therein.
Figure 4:
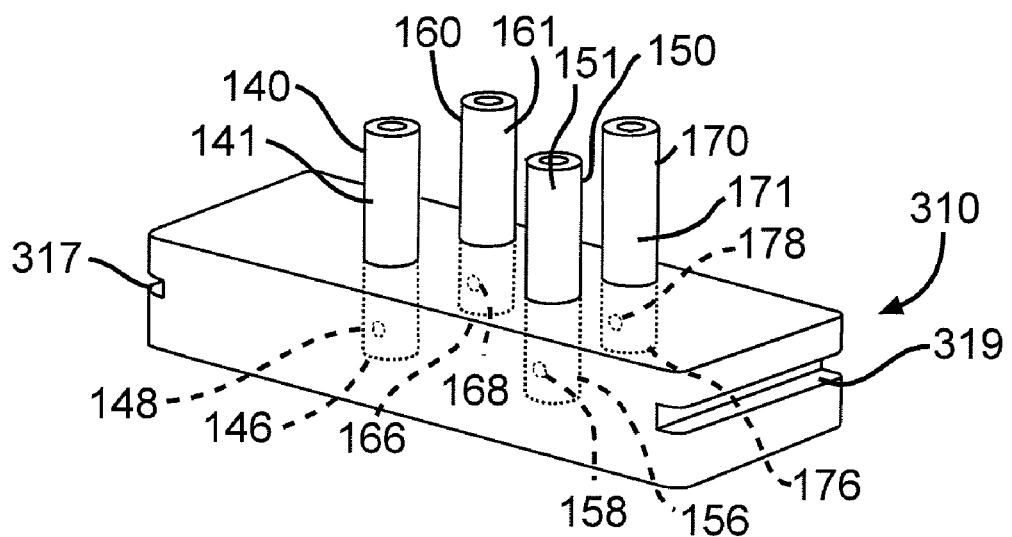
FIG. 4 is a perspective view of the feedthrough adapter holder and conductive connectors of FIG. 3.

FIG. 2 is a perspective view of a feedthrough adapter holder used in making the header assembly; FIG. 3 is a cross-sectional view of the feedthrough adapter holder of FIG. 2, with conductive connectors of the header assembly fitted within through holes therein; and FIG. 4 is a perspective view of the feedthrough adapter holder and connectors of FIG. 3. A feedthrough adapter holder 310 is provided comprising a plate shaped body 312 including an upper surface 314, a lower surface 316, a side wall 318, and through holes 340, 350, 360, and 370 extending from the upper surface 314 to the lower surface 316. Feedthrough adapter holder 310 may consist essentially of polysulfone polymeric, or polyetheretherketone polymeric.

Four conductive connectors 140, 150, 160, and 170 are provided and press-fittingly disposed respectively in through holes 340, 350, 360, and 370. Connector 140 is comprised of an outer surface 141, a distal end 142 including a distal bore 143, a central region 145, and a proximal end 146 including a proximal bore 147. Connectors 150, 160, and 170 are similarly structured. The through holes 340, 350, 360 and 370 in feedthrough adapter holder 310 are provided with diameters sized to enable a mild press fit of the connectors disposed therein. The connectors 140, 150, 160 and 170 are first press fitted into feedthrough adapter holder 310 such that each is engaged with the holder at its central region, e.g., connector 140 is engaged with through hole 340 at central region 145. Feedthrough adapter holder may further comprise grooves 317 and 319 at opposed ends thereof. These grooves are provided for engagement with a tool (not shown) used during press fitting of the connectors 140, 150, 160 and 170 into the feedthrough adapter holder 310, for subsequently moving the adapter 310 with respect to the connectors and for removing the adapter 310 from the finished header assembly at the end of fabrication.

The feedthrough adapter holder 310 serves to precisely locate the connectors 140, 150, 160 and 170 fitted therein during subsequent header assembly fabrication steps, and is particularly useful for header assemblies comprised of a high number of conductive subassemblies closely spaced in a dense array. One such fabrication step is the drilling of through holes in each of the connectors. Referring again to FIG. 3, with the connectors 140, 150, 160 and 170 engaged with feedthrough adapter holder 310 at their central regions, through holes 148, 158, 168, and 178 are drilled in the connectors extending from the respective outer surfaces 141, 151, 161, and 171 thereof into the proximal bores thereof. The drilling of through holes 148, 158, 168 and 178 is preferably performed by electrical discharge machining (EDM) or laser drilling, with the feedthrough adapter holder 310 and connectors 140, 150, 160 and 170 held in a high precision fixture (not shown). In one embodiment, the connectors are made of titanium, with a cylindrical shape, a length of about 0.13 inches, a diameter of about 0.03 inches, distal and proximal bores of about 0.017 inches in diameter, and a through hole of about 0.01 inches in diameter. Through holes 148, 158, 168 and 178 are useful in a process of laser welding the connectors to conductor wires, as will be described subsequently herein.

After the drilling of through holes 148, 158, 168 and 178, the connectors 140, 150, 160 and 170 are displaced along their central axes within the feedthrough adapter holder, as shown in FIG. 4, and in FIG. 3 in phantom. Feedthrough adapter holder 310 is then engaged with the proximal ends 146, 156, 166, and 176 of the connectors 140, 150, 160 and 170, including the through holes 148, 158, 168 and 178.

Figure 4A:
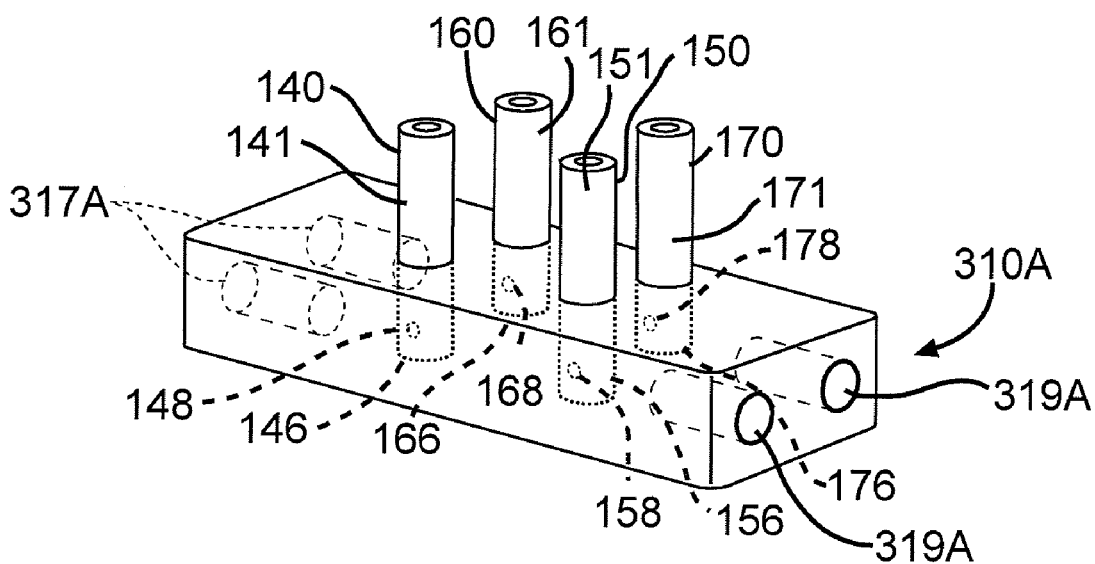
FIG. 4A is a perspective view showing a plurality of conductive connectors being supported by an alternate embodiment of a feedthrough adapter holder.

FIG. 4A illustrates an alternate embodiment of a feedthrough adapter holder 310A provided with a pair of spaced apart horizontally aligned bores 317A and 319A at its opposite ends. The bores 317A, 319A serve a similar function as the grooves 317, 319 by providing for engagement with a tool and for removing the adapter 310A from the finished header assembly at the end of fabrication.

Figure 5:
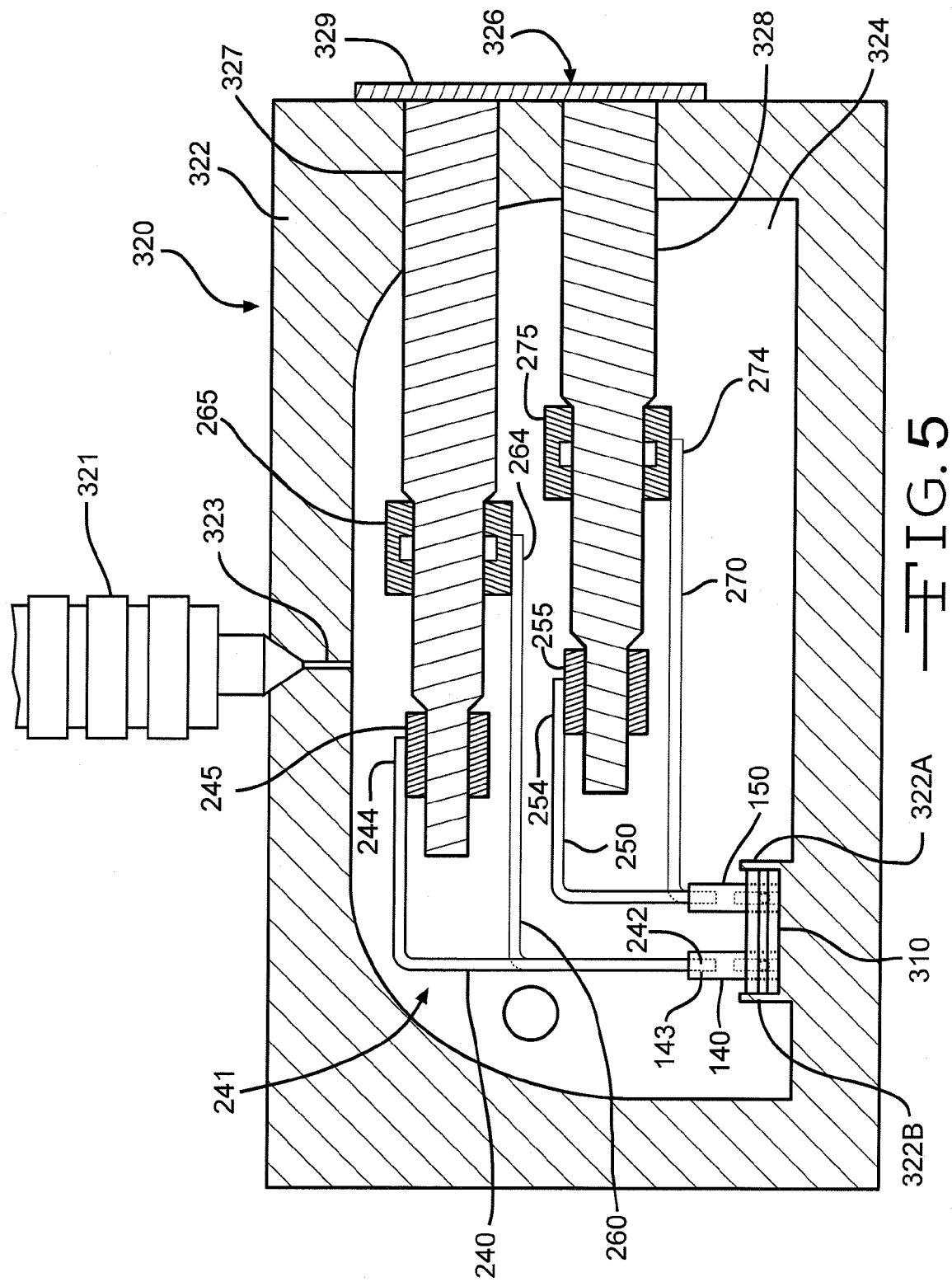
FIG. 5 is a cross-sectional view of conductor subassemblies of the header assembly placed in a mold, prior to molding the header body of the header assembly.

Intermediate conductor wires to be joined to the connectors are then provided. This is best understood with reference to FIGS. 1 and 5, which depict the intermediate conductor wires after the overall fabrication of the conductive subassemblies is completed. Conductor wires 240, 250, 260, and 270 are joined to connectors 140, 150, 160, and 170, respectively. Each of the conductor wires is comprised of a distal end, and a proximal end. The proximal ends of the conductor wires are disposed in the distal bores of the respective connectors. For example, proximal end 242 of conductor wire 240 is disposed in distal bore 143 of connector 140.

The conductor wires are then joined to their respective connectors. The joining is preferably performed by laser welding the conductor wire proximal ends to the distal ends of the connectors. Alternatively, the joining may be accomplished by a press fit of the conductor wire proximal ends in the distal bores.

The partial subassemblies consisting of conductor wires 240, 250, 260 and 270 and connectors 140, 150, 160 and 170 disposed within feedthrough adapter holder 310 are then placed in a fixture (not shown) so that the distal ends of the conductor wires can be joined to terminals. The conductor wires 240, 250, 260 and 270 are preferably provided preformed into their respective desired shapes to be supported within the polymeric header body 110 (see FIG. 1) prior to the step of positioning the conductor wires in the fixture. Alternatively, the conductor wires 240, 250, 260 and 270 may be formed into the desired shapes when the feedthrough adapter holder 310 has been secured in the fixture.

With the conductor wires formed and secured in the fixture in their respective desired shapes to be supported within the polymeric header body 110, terminals to be joined to the distal ends of conductor wires 240, 250, 260 and 270 are then provided. Suitable terminals, or terminal blocks, are as described in paragraphs 0029-0033 of the aforementioned U.S. Patent Application Pub. No. 2004/0093038 of Biggs et al. Terminals 245, 255, 265, and 275 are joined to the respective distal ends 244, 254, 264, and 274 of conductor wires 240, 250, 260, and 270 by resistance welding, laser welding, or another suitable joining process. The exemplary completed conductor subassembly 241 comprises the connector 140, conductor wire 240, and terminal 245. In the preferred embodiment, connector 140, wire 240, terminal 245, and the corresponding components of the other conductor subassemblies are made of titanium. Alternatively, these components may be made of MP35N, stainless steel, palladium or another high purity biocompatible metal.

Referring again to FIG. 5, the entire cluster of conductor subassemblies temporarily joined by the feedthrough adapter holder 310 are removed from the fixture (not shown), and placed in a mold 320. The mold comprises a mold body 322 and a mold cavity 324, and is formed in the desired shape of the molded header body 110. Of particular note is that the mold body 322 has spaced apart upstanding webs 322A and 322B that contact opposite sides of the holder 310. These webs 322A, 322B occupy space immediately adjacent to the grooves 317, 319 in the holder for later accessing the grooves for removing the holder from the connectors 140, 150.

A conductor lead mold insert 326 is preferably provided which includes two connector lead plugs 327 and 328 joined to a base plate 329. The use of connector mold insert 326 forms openings 112 and 114 (see FIG. 6) in the molded header body 110 in the shape of lead plugs 327 and 328, which are dimensioned substantially the same as connector lead 24 of FIG. 1. In this manner, the connector lead openings 112 and 114 are formed as part of the molding process, and do not need to be separately bored in a subsequent step.

The polymeric header body is then molded by injecting a polymeric melt from nozzle or die 321 through port 323 into the mold cavity 324. The polymeric melt fills mold cavity 324, thereby forming a monolithic structure surrounding the conductor subassemblies and the mold inserts therein. Suitable moldable polymeric materials for header body 110 include urethanes, such as e.g., TECOTHANE®, an aromatic polyether-based thermoplastic polyurethane sold by the Thermedics Polymeric Products Company of Wilmington, Mass.

Figure 6:
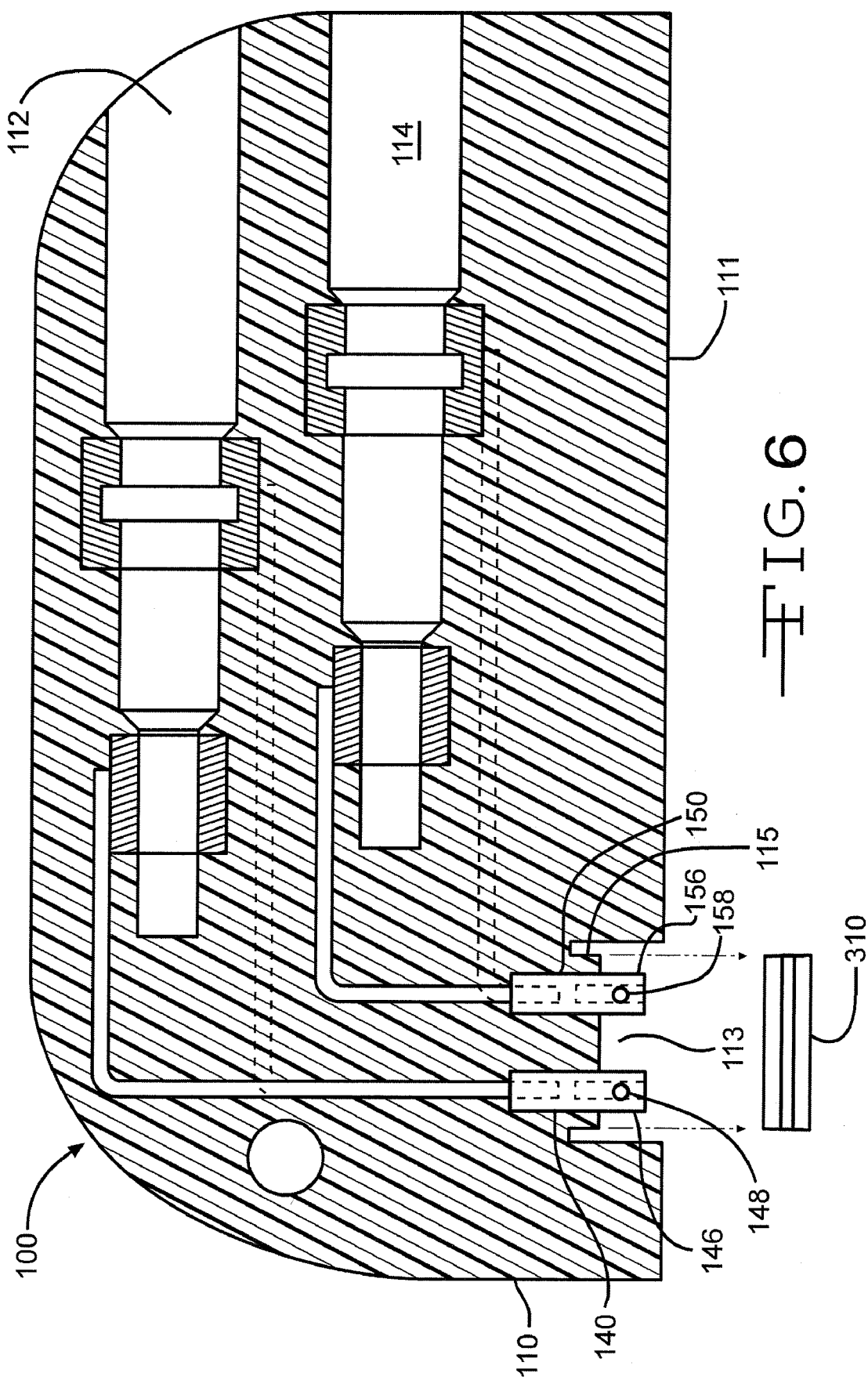
FIG. 6 is a cross-sectional view of one finished header assembly including the conductor subassemblies and the molded header body, and also showing the feedthrough adapter holder being removed from the conductive connectors of the header assembly.

FIG. 6 is a cross-sectional view of one finished header assembly 100 including the conductor subassemblies and the monolithic molded header body 110 after the header assembly has been removed from the mold 320, the conductor lead mold insert 326 has been removed from header body 110, and the feedthrough adapter holder 310 has been removed from the proximal ends of the connectors. The holder 310 is removed from the connectors by engaging the opposed grooves 317, 319 in its sidewall 318 with a grabber tool (not shown) and pulling in a downwardly direction. Access to the grooves 317, 319 is by means of the space previously occupied by the webs 322A, 322B of the mold body 322.

The resulting gap 113 in the header body 110 has an extended boss 115 protruding downwardly from the bottom surface 111 of the insulative material. Since it is important to have the proximal bores of the connectors mate properly with the feedthrough wires of the implantable device, it is preferable that the connectors of the header assembly be precisely located and rigidly supported by the body of the header assembly. In that respect, the extended boss 115 provides improved support at the distal end and central region of each of the connectors while the proximal connector ends including the proximal bores and the through holes therein are disposed within the gap. For example, proximal end 146 of connector 140 is disposed in gap 113, with the through hole 148 therein clearly exposed. This structure is useful in performing a laser welding process to join the connectors of the header assembly to the feedthrough wires of the implantable device, as will be explained presently.

It is to be understood that the header assemblies, subcomponents, and associated tools described and shown herein are exemplary. The molded header can have a myriad of different shapes only limited by the design specifications of the associated medical device and its intended use. Additionally, it is not required that the header assemblies shown in the accompanying drawings have any particular number of conductor subassemblies, and are thus not limited to connection to implantable devices comprising any particular number of feedthrough wires. While the header assemblies of the present invention are particularly useful when dense arrays of conductor subassemblies are required therein for connection to numerous feedthrough wires, the instant header assemblies may be comprised of only a single conductor subassembly.

In one exemplary embodiment (not shown), the header assembly is comprised of six conductor subassemblies with the proximal ends of the six connectors exposed in gap 113. The six conductors are preferably disposed in a hexagonal arrangement. In another exemplary embodiment, the header assembly is comprised of eight conductor subassemblies with the proximal ends of the eight connectors exposed in gap 113. The eight conductors are preferably disposed in an arrangement of two groups of four. The tooling and fabrication methods for this embodiment are shown in FIGS. 9 to 15, and will be described subsequently herein.

Figure 7:
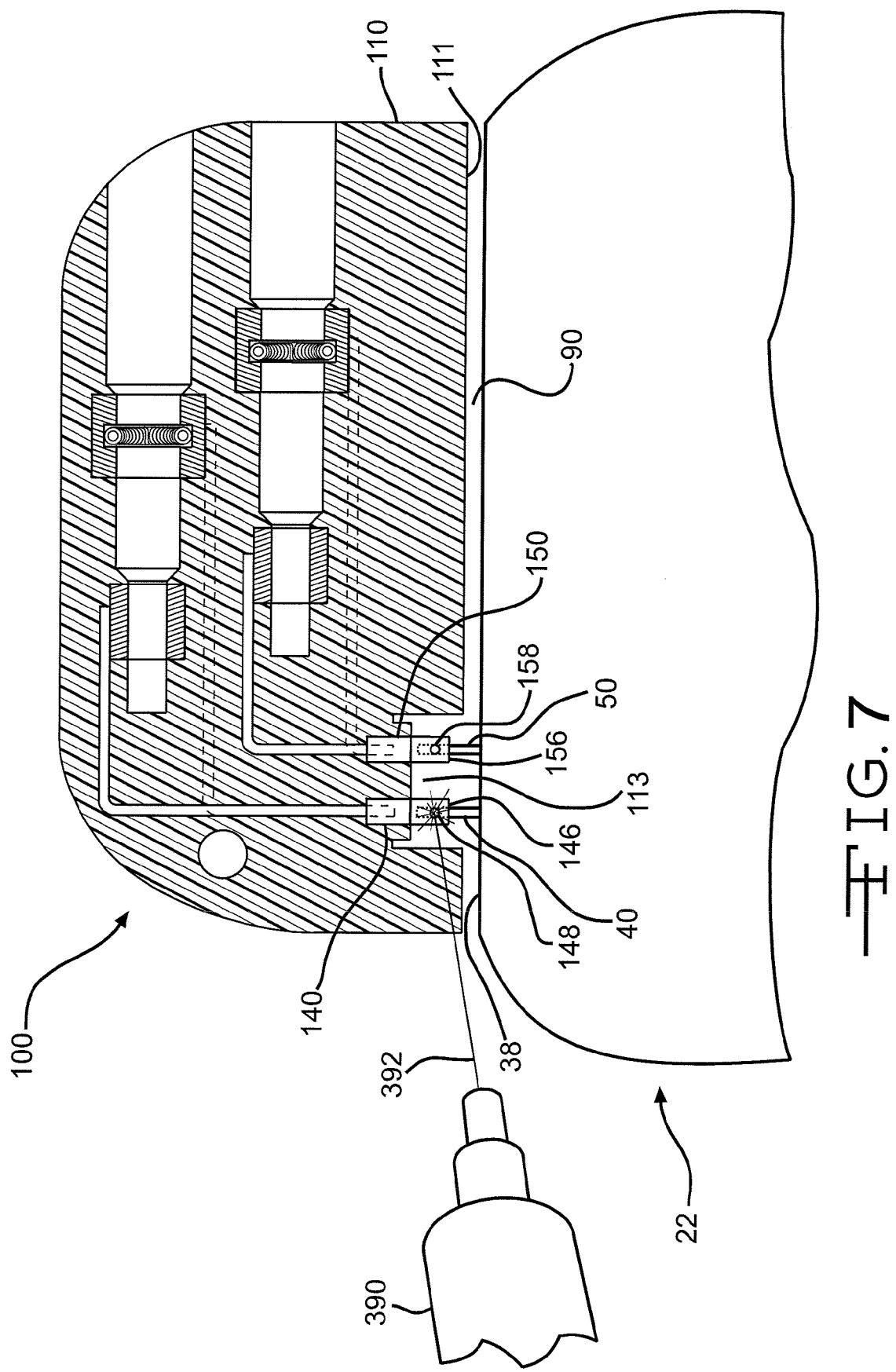
FIG. 7 is a schematic illustration of one method for laser welding the feedthrough wires of the implantable medical device to the connectors of the conductor subassemblies of the header assembly.

The header assembly 100 of FIG. 6 is connectable to an implantable device. In general, a method for connecting header assembly 100 to an implantable device includes the steps of connecting the conductor subassemblies therein to the feedthrough wires of the device, and sealing the header assembly to the housing of the device. FIG. 7 is a schematic illustration of one method for laser welding the feedthrough wires to the connectors of the conductor subassemblies. The method begins by positioning header assembly 100 proximate to the implantable device 22 in a fixture (not shown). The feedthrough wires of the device 22 are now disposed in the proximal bores of the connectors of the conductor subassemblies. (For example, feedthrough wire 40 is disposed in connector 140, and feedthrough wire 50 is disposed in connector 150.) Bottom surface 111 of the insulative body 110 is proximate to the upper surface 38 of the wall of the housing 110, with an interstice 90 formed there between. Interstice 90 is depicted in FIG. 7 for illustrative purposes and may be considerably narrower than shown.

Figure 8:
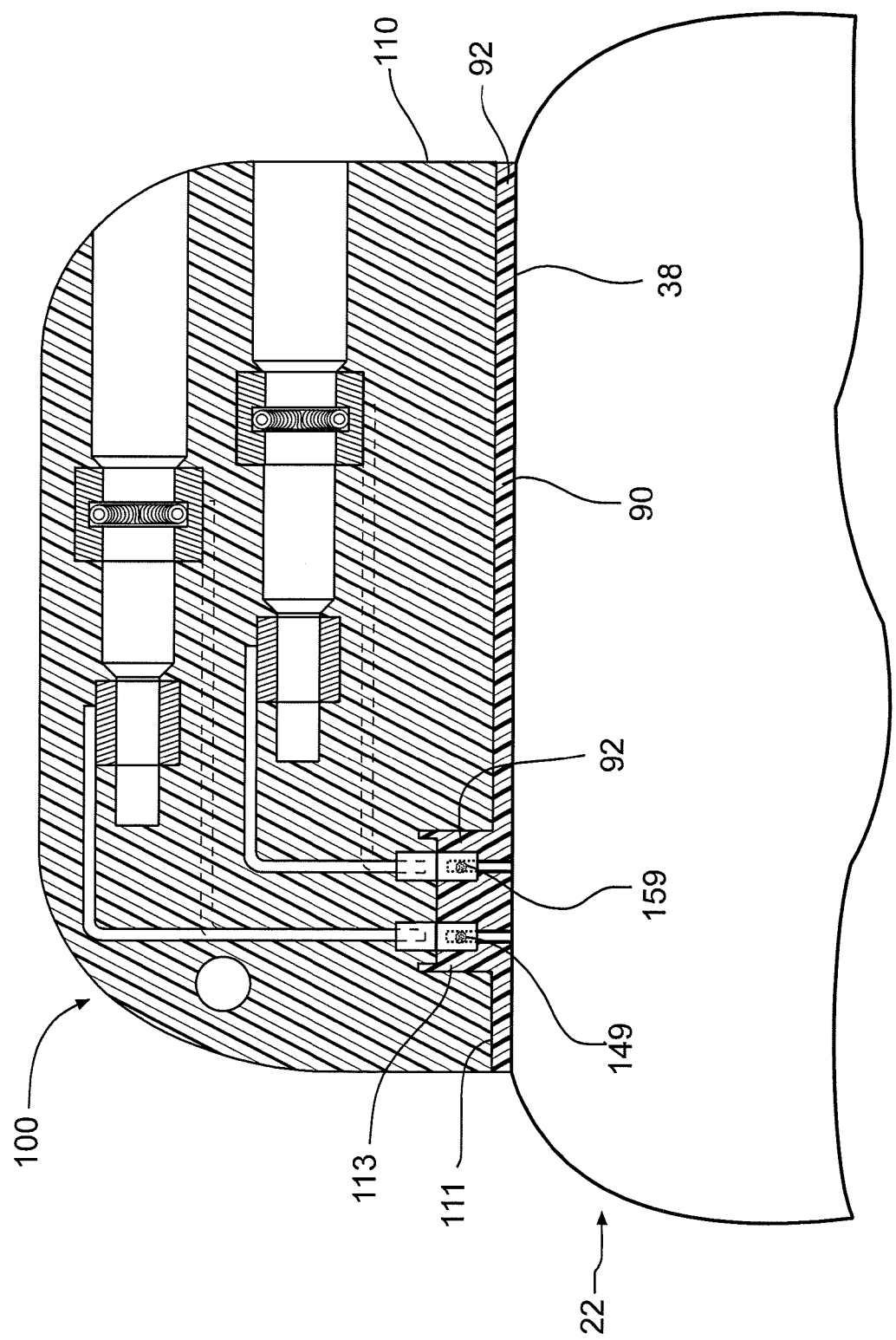

With the header assembly 100 positioned as shown with respect to the implantable device 22, the feedthrough wires of the device are joined to the connectors of the header assembly 100, preferably by laser welding. This is done by directing a laser beam through the through holes in the proximal bores of the connectors onto the respective feedthrough wires disposed therein. For example, as depicted in FIG. 7, laser 390 directs laser beam 392 into through hole 148 of connector 140 and onto feedthrough wire 40. This results in the connector wall material surrounding the through hole 148 melting along with the wire, thereby welding the connector 140 to the feedthrough wire 40. Referring also to FIG. 8, welds 149 and 159 are made between their respective connectors and feedthrough wires. Laser 390 is mounted on a movable fixture (not shown) so that the laser beam 392 may be sequentially directed to each of the through holes in the connectors. It will be apparent that multiple lasers could be used to achieve the same result.

Referring to FIG. 1, it can be seen that the through holes in the connectors 140, 150, 160, and 170 are all exposed on the proximal side 115 of the header assembly 100. Thus, with proper manipulation of laser 390, all of the connectors can be welded to the respective feedthrough wires 40, 50, 60 and 70. However, in embodiments of the header assembly that are comprised of a greater number of connector assemblies, such as the exemplary six or eight connector assemblies, some of the connectors may obstruct others when viewed from only one side of the header assembly. In such embodiments, it is beneficial to position some of the connectors with their respective through holes facing the proximal side 115, and others facing the distal side 117 of the header assembly 100. In this configuration, the laser 390 performs a first set of welds while positioned on the proximal side 115 and a second set of welds while positioned on the distal side of the header assembly 100.

With the connectors joined to their respective feedthrough wires, the header assembly 100 is then secured to the implantable device 22. In one embodiment, a curable liquid sealant is discharged into the interstice 90 between the header assembly 100 and the implantable device 22. Referring to FIG. 8, cured liquid sealant 92 fills interstice 90 and gap 113 between assembly 100 and device 22. This seals the welded connectors and feedthrough wires embedded therein, and joins assembly 100 to device 22. In one embodiment, the cured liquid sealant 92 may consist essentially of an organopolysiloxane, also known generally as "silicone rubber." One suitable organopolysiloxane is Med-4211, sold by the Nusil Company of Carpiytia, Calif.

Figure 9:
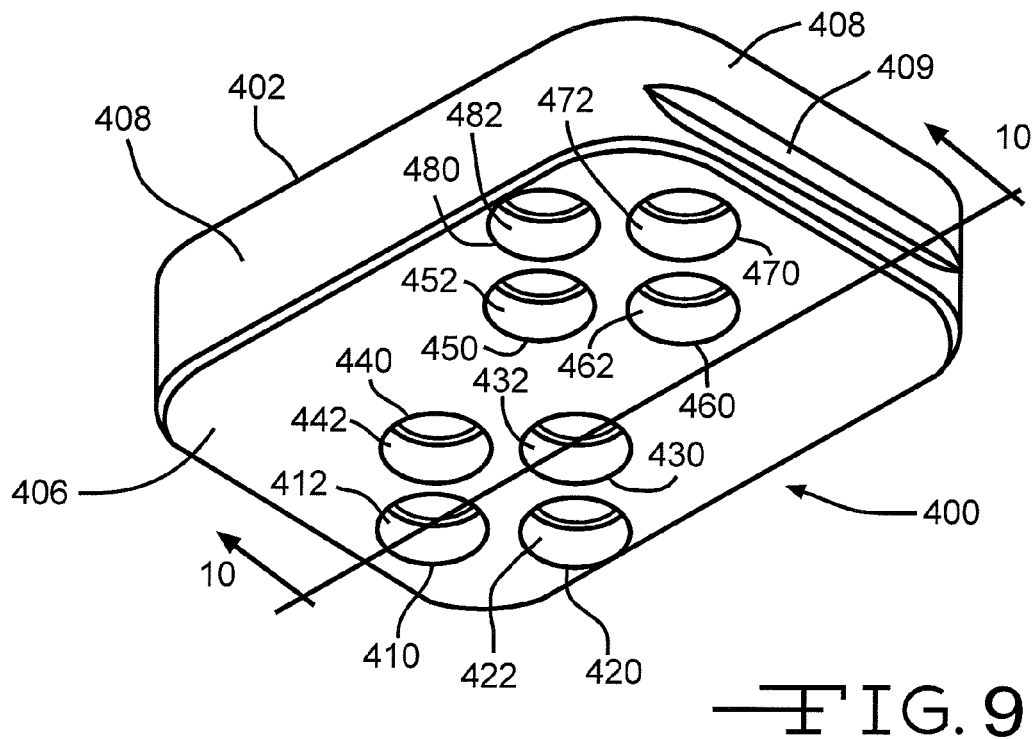
FIG. 9 is a lower perspective view of an alternative feedthrough adapter holder configured to support the conductive connectors of a high density array of conductor subassemblies during the fabrication of the header assembly.
Figure 10:
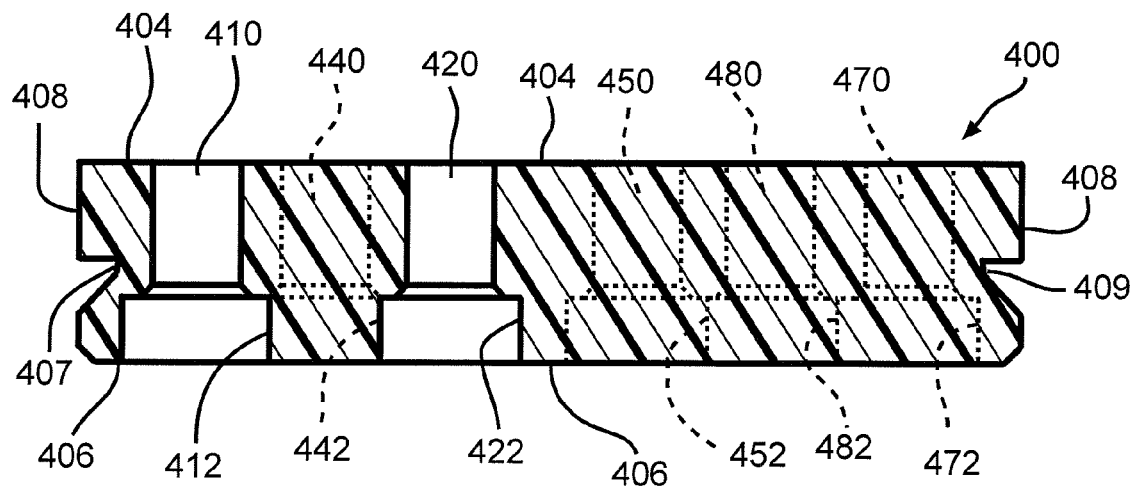
FIG. 10 is a cross-sectional view of the feedthrough adapter holder taken along line 10-10 of FIG. 9.

The tooling and methods of making such a header assembly with a molded boss, and also a header assembly comprised of a more complex array of conductor subassemblies will now be described with reference to FIGS. 9 to 14. FIG. 9 is a lower perspective view of an alternative feedthrough adapter holder 400 configured to support the connectors of a high density array of conductor subassemblies during fabrication of the header assembly. FIG. 10 is a cross-sectional view of the feedthrough adapter holder 400 taken along line 10-10 of FIG. 9. Feedthrough adapter holder 400 has a plate shaped body 402 including an upper surface 404, a lower surface 406, a side wall 408, and through holes 410, 420, 430, 440, 450, 460, 470, and 480 extending from the upper surface 404 to the lower surface 406. In one exemplary embodiment in which the implantable device (not shown) is comprised of eight feedthrough wires arranged in two groups of four wires, the through holes are provided in the corresponding arrangement of holes 410, 420, 430 and 440 and holes 450, 460, 470 and 480, as shown in FIG. 9.

Feedthrough adapter holder may include counter bores 412, 422, 432, 442, 452, 462, 472 and 482 in respective holes 410, 420, 430, 440, 450, 460, 470 and 480. The counter bores 412, 422, 432, 442, 452, 462, 472 and 482 are adapted to receive small pedestals protruding from a mold insert used during the header body molding process, as will be explained subsequently herein.

Feedthrough adapter holder 400 may further comprise grooves 407 and 409 at opposed ends thereof. These grooves are provided for engagement with a tool (not shown) used during press fitting of connectors into the feedthrough adapter holder 400, for subsequently moving the adapter 400 with respect to the connectors, and for removing the adapter 400 from the finished header assembly 500 at the end of fabrication.

Figure 11:
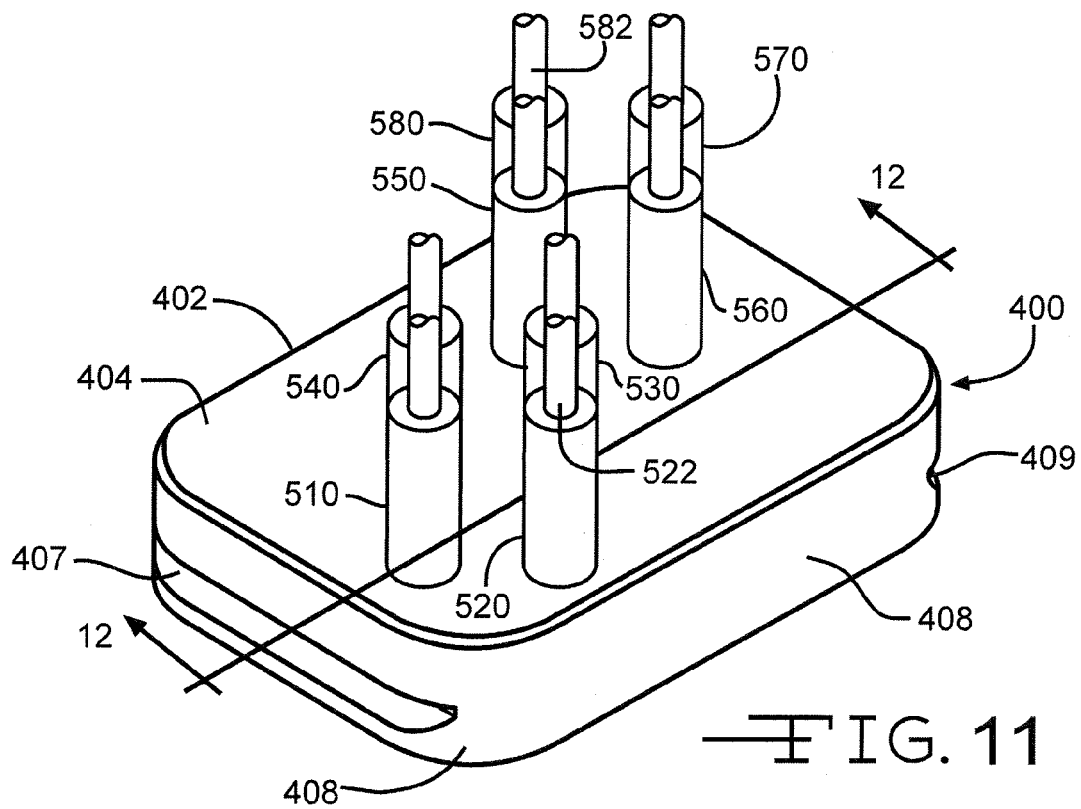
FIG. 11 is an upper perspective view of the feedthrough adapter holder of FIG. 9, including connectors of the header assembly fitted within through holes therein.
Figure 12:
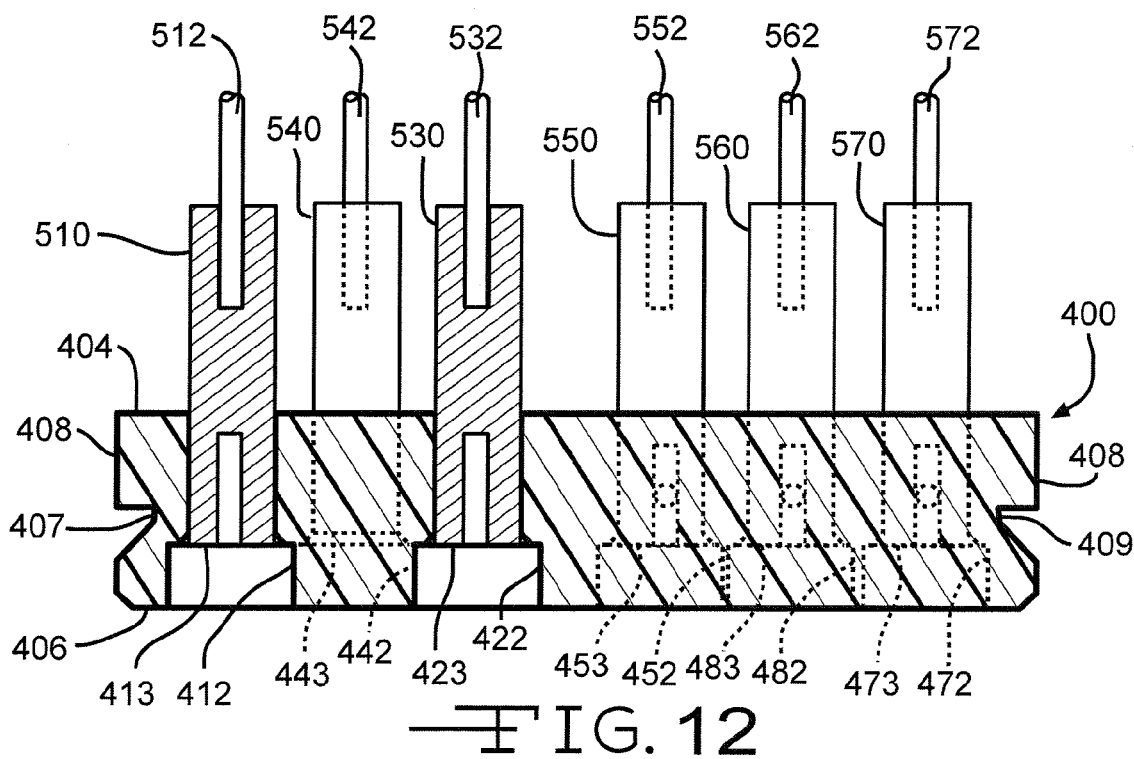
FIG. 12 is a cross-sectional view of the feedthrough adapter holder and conductive connectors taken along line 12-12 of FIG. 11.

FIG. 11 is an upper perspective view of the feedthrough adapter holder 400 of FIG. 9, including connectors of the header assembly press fitted within through holes therein. FIG. 12 is a cross-sectional view of the feedthrough adapter holder 400 and conductive connectors taken along the line 12-12 of FIG. 11. Connectors 510, 520, 530, 540, 550, 560, 570, and 580 are moved into a press-fit relationship in the respective through holes 410, 420, 430, 440, 450, 460, 470, and 480. Each of connectors 510, 530, 540, 550, 560 and 570 is comprised of an outer surface, a distal end including a distal bore, a central region, and a proximal end including a proximal bore, as described previously herein for connectors 140, 150, 160 and 170 of FIGS. 2 to 4.

In FIGS. 11 and 12, connectors 510, 530, 540, 550, 560 and 570 are shown after their respective through holes have been drilled in their proximal bores, and after each has been joined to the respective conductor wires 512, 532, 542, 552, 562 and 572. Feedthrough adapter holder 400 has been displaced downwardly along the connectors 520, 530, 540, 550, 560 and 570 such that the proximal ends of the connectors are contiguous with the upper ends of counter bores 412, 422, 442, 452, 472 and 482 of feedthrough adapter holder 400. (Counter bore upper ends 413, 423, 443, 453, 473, and 483 are depicted in FIG. 12.)

Figure 15:
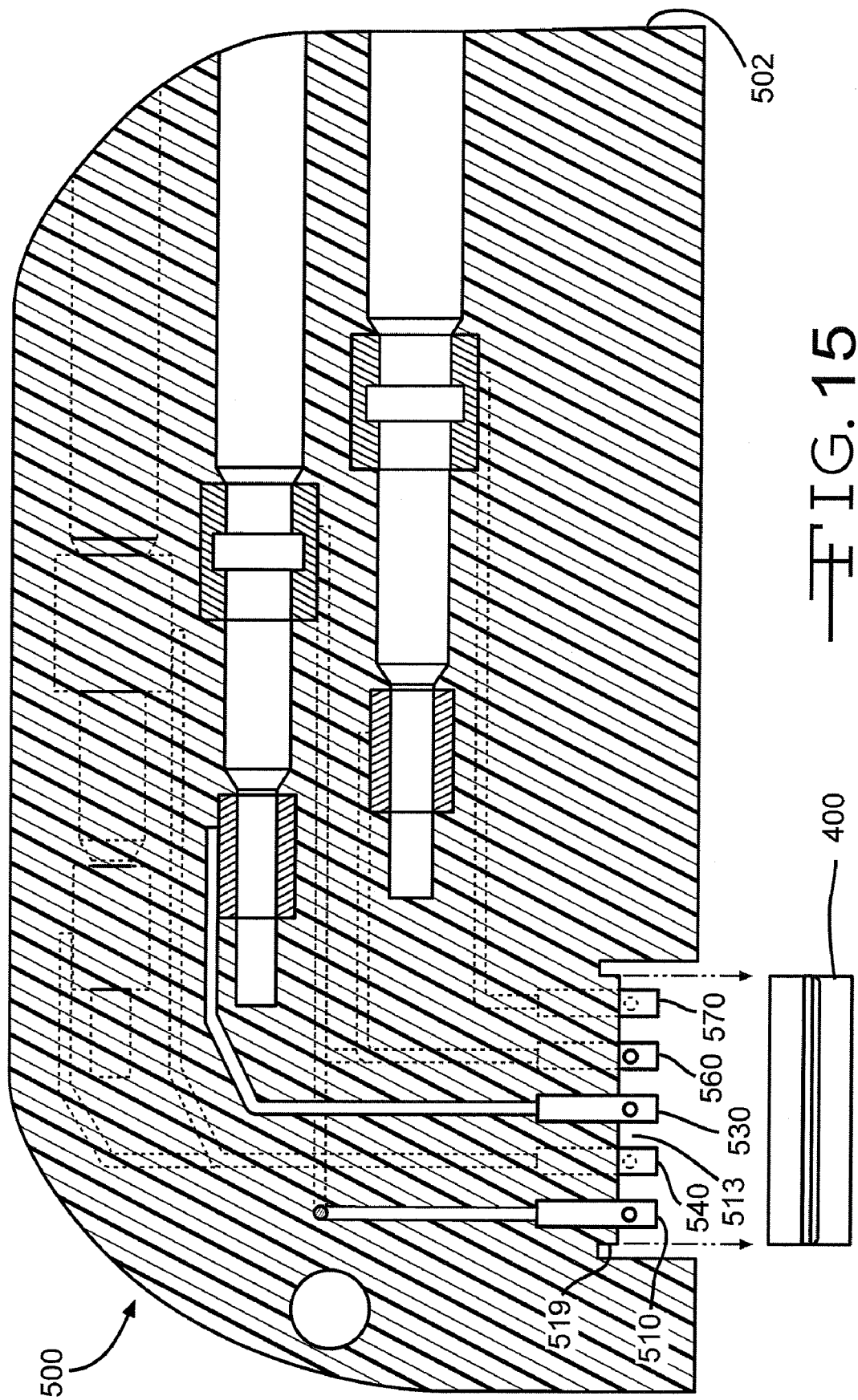
FIG. 15 is a cutaway view of a finished header assembly made with the tools and methods of FIGS. 9 to 14.

Each of the connectors 510, 520, 530, 540, 550, 560, 570 and 580 and conductor wires 512, 522, 532, 542, 552, 562, 572 and 582, along with corresponding terminals (not shown) form a set of eight conductor subassemblies as previously described herein. With fabrication of the conductor assemblies complete, and with feedthrough adapter holder 400 having been located in the desired position on the connectors 510, 520, 530, 540, 550, 560, 570 and 580 for the header body molding process, the eight conductor assemblies and the feedthrough adapter holder are placed in a mold as described previously herein. Preferably, an additional mold insert is provided which enables the formation of an extended boss 519 protruding downwardly into gap 513 on the header body 502 of header assembly 500 (FIG. 15).

Figure 13:
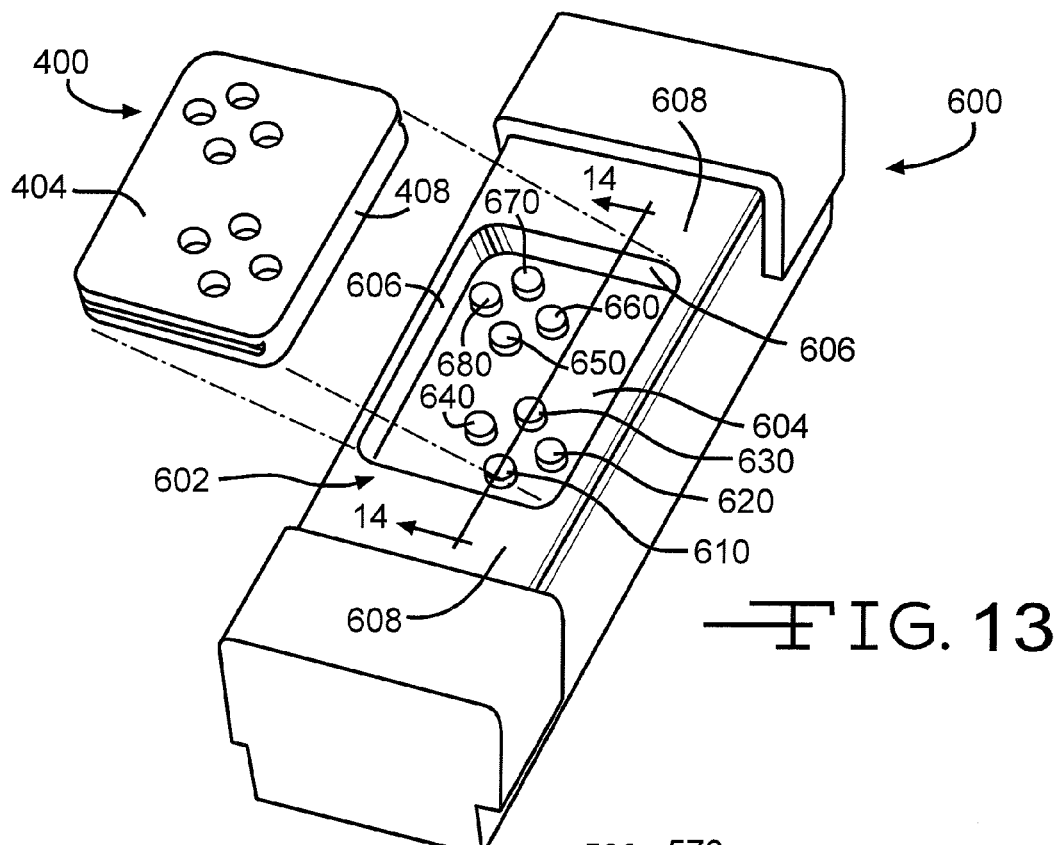
FIG. 13 is a perspective view of a mold insert configured to accept the feedthrough adapter holder of FIGS. 9 to 12 in a cavity therein, wherein the mold insert forms a part of the mold during the header body molding process.
Figure 14:
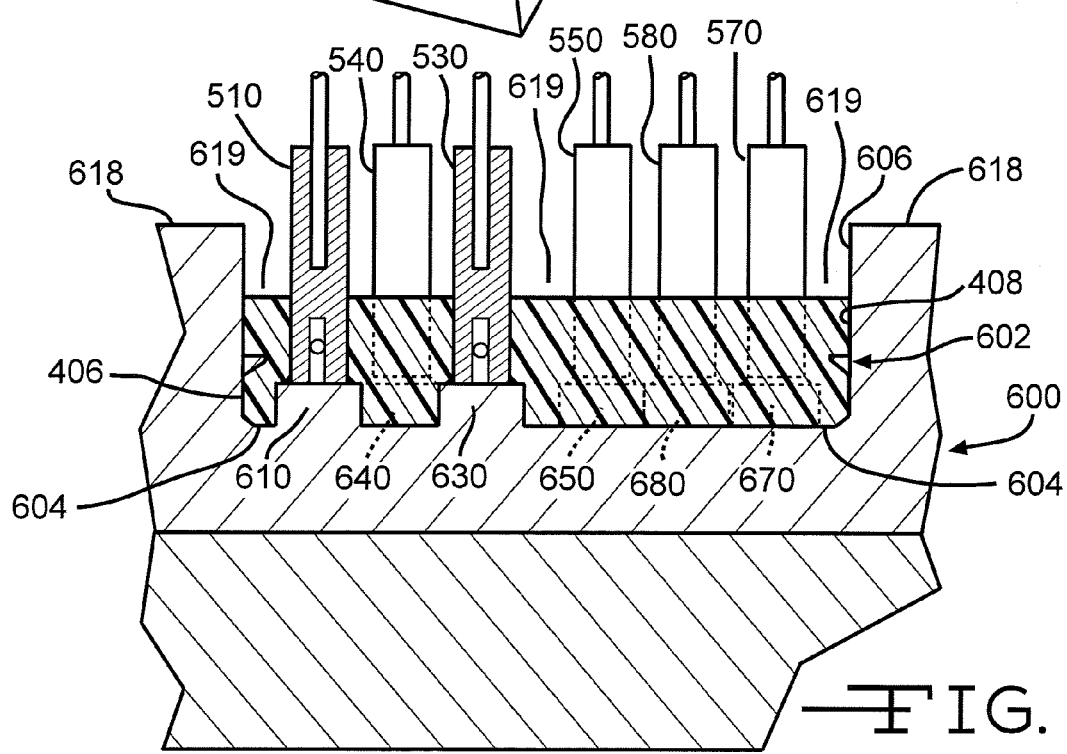
FIG. 14 is a cross-sectional view of the mold insert and feedthrough adapter holder taken along line 14-14 of FIG. 13.

Referring to FIGS. 13 and 14, mold insert 600 is configured to accept the feedthrough adapter holder 400 of FIGS. 9 to 12 in a cavity therein. The mold insert 600 forms part of the mold (not shown) during the header body molding process. Mold insert 600 comprises a recessed cavity 602 comprising a bottom surface 604 and a side surface 606 terminating at an upper surface 608. Recessed cavity 602 is dimensioned such that feedthrough adapter holder 400 is a sliding fit when disposed therein, with the connectors of the connector assemblies fitted in the respective through holes of holder 400. (For the sake of simplicity of illustration, the connectors and connector wires are not depicted in FIG. 13, but are present as shown in FIG. 11.)

During the molding process, feedthrough adapter holder 400 is disposed in recessed cavity 602 such that the bottom surface 604 of recessed cavity 602 is contiguous with the lower surface 406 of the feedthrough adapter holder 400, and the side surface 606 of the recessed cavity 602 is contiguous with the side wall 408 of the feedthrough adapter holder 400. If feedthrough adapter holder 400 and recessed cavity 602 are dimensioned such that upper surface 404 of the holder 400 and the upper surface 608 of the mold insert 600 are coplanar, no extended boss 519 will be formed on header body 502. Thus, in order to form the extended boss 519, the recessed cavity 602 is of a sufficient depth such that upper surface 404 of the holder 400 is located below the upper surface 608 of the mold insert 600 and within the recessed cavity 602. During the molding process, the polymeric melt fills boss cavity 619, thereby forming extended boss 519.

To ensure precise location of the connectors 510, 520, 530, 540, 550, 560, 570 and 580, mold insert 600 may be provided with corresponding pedestals 610, 620, 630, 640, 650, 660, 670 and 680, which are disposed within respective counter bores 412, 422, 432, 442, 452, 462, 472 and 482 (see FIGS. 9 and 10). During the molding process, the upper surfaces of pedestals 610, 620, 630, 640, 650, 660, 670 and 680 are contiguous with the proximal ends of connectors 510, 520, 530, 540, 550, 560, 570 and 580.

FIG. 15 is a cutaway view of a finished header assembly 500 made with the tools and methods of FIGS. 9 to 14. Header assembly 500 is comprised of a molded polymeric body 502 as a monolithic structure including an extended boss 519, as described previously. Much of the general structure of header assembly 500 is similar to the header assembly 100 of FIG. 1, with the main difference being that the exemplary header assembly 500 is comprised of eight conductor subassemblies described previously (not all of which are visible in the drawing.)

Header assembly 500 is connected to an implantable device (not shown) by the methods described previously herein. The implantable medical device is comprised of eight feedthrough wires extending from the control circuitry and through the wall of the housing. They are arranged in two groups of four wires to match the corresponding arrangement of connectors 510, 520, 530, 540, 550, 560, 570 and 580 of the header assembly 500. Header assembly 500 is comprised of a proximal side and a distal side. In order for laser welding of the connectors 510, 520, 530, 540, 550, 560, 570 and 580 to the feedthrough wires of the implantable device to be most effectively performed, the through holes in the proximal bores of a first group of four wires are viewable from the proximal side of the header assembly, and the through holes in the proximal bores of a second group of four wires are viewable from the distal side of the header assembly. Referring again to FIG. 15, the through holes of connectors 510, 520 (not shown), 530, and 560 are viewable and are welded from the proximal side of the header assembly 500 and the through holes of connectors 570, 580 (not shown), 550 (not shown) and 540 are viewable and are welded from the distal side thereof.

In another exemplary embodiment (not shown), a header assembly made according to the instant method may be comprised of six conductor subassemblies, the connectors of which may be arranged in a hexagonal array. In this embodiment, three of the through holes of the connectors may be viewable and weldable from the proximal side of the header assembly, and three of the through holes of the connectors may be viewable and weldable from the distal side of the header assembly. It is also to be understood that the header assembly made according to the instant method may be comprised of only a single conductor subassembly with the connector embedded in the extended boss of the header body. It is not required that the header assembly be comprised of a dense array of conductor subassemblies.

It is, therefore, apparent that there has been provided, in accordance with the present invention, a header assembly for connecting an implantable medical device to at least one conductor lead terminating within a patient intended to be assisted by the medical device, and methods for making the header assembly, and for connecting the header assembly to the implantable medical device.

While this invention has been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of the appended claims.

What is claimed is:

1. A header assembly for connecting an implantable medical device to at least one conductor lead terminating within a patient intended to be assisted by the medical device comprising a housing containing control circuitry, at least one electrical energy storage device, and at least one feedthrough wire extending from the control circuitry and through a wall of the housing, the header assembly comprising:

a) an insulative body that is mountable on the housing of the medical device; and
b) at least one conductor subassembly comprising:
   i) a terminal supported by the insulative body, wherein the terminal is directly connectable to the at least one conductor lead;
   ii) an intermediate conductor comprising a distal conductor end connected to the terminal, and a proximal conductor end; and
   iii) a connector comprising an outer surface, a distal connector end including a distal connector bore, a proximal connector end including a proximal connector bore, a central connector region that prevents communication between the distal and proximal connector bores, and a through hole extending from the outer surface into the proximal connector bore, wherein the distal end of the connector is supported by the insulative body, the proximal end of the intermediate conductor is disposed within the distal connector bore, and the proximal connector bore is connectable to the at least one feedthrough wire of the implantable medical device.

2. The header assembly of claim 1 comprising a plurality of conductor subassemblies being connectable to a plurality of feedthrough wires extending from the control circuitry and through a wall of the housing of a medical device.

3. The header assembly of claim 2 wherein the insulative body is comprised of an extended boss supporting the distal end and the central region of each of the connectors of the plurality of conductor subassemblies.

4. The header assembly of claim 1 wherein the insulative body is of a molded polymeric.

5. The header assembly of claim 1 wherein the terminal, the intermediate conductor, and the connector of the at least one conductor subassembly consist essentially of titanium or MP35N.

6. The header assembly of claim 1 wherein the connector is of a cylindrical shape.

7. The header assembly of claim 1 wherein the medical device is selected from the group consisting of a hearing assist device, neurostimulator, cardiac pacemaker, drug pump, cardiac defibrillator, and an obesity control device.

8. The header assembly of claim 1 wherein a gap is provided in the bottom surface of the insulative body, and wherein the proximal end of the connector including the proximal bore and the through hole therein is disposed within the gap.

9. A method for connecting a header assembly to an implantable medical device, comprising the steps of:

a) providing the implantable medical device comprising a housing containing control circuitry, at least one electrical energy storage device, and at least one feedthrough wire extending from the control circuitry and through a wall of the housing;
b) providing the header assembly comprised of an insulative body that is mountable on the housing of the medical device, and at least one conductor subassembly comprising:
   i) a terminal supported by the insulative body;
   ii) an intermediate conductor comprising a distal conductor end connected to the terminal, and a proximal conductor end; and
   iii) a connector comprising an outer surface, a distal connector end including a distal connector bore, a proximal connector end including a proximal connector bore, a central connector region that prevents communication between the distal and proximal connector bores, and a through hole extending from the outer surface into the proximal connector bore, wherein the distal end of the connector is supported by the insulative body, the proximal end of the intermediate conductor is disposed within the distal connector bore, and the proximal end of the connector including the through hole is exposed in a recess in the bottom surface of the insulative body;

c) positioning the header assembly proximate to the implantable device wherein the at least one feedthrough wire is disposed in the proximal connector bore of the conductor subassembly; and d) directing at least one laser beam into the through hole in the proximal connector bore and onto the feedthrough wire disposed therein, to thereby connect the feedthrough wire of the implantable medical device to the connector of the conductor subassembly.

10. The method of claim 9 further comprising the step of sealing the insulative body of the header assembly to the housing of the implantable medical device.

11. The method of claim 10 wherein after the step of positioning the header assembly proximate to the implantable device, an interstice is present between the insulative body proximate to the housing of the implantable medical device, and then filling the interstice with a curable liquid sealant.

12. The method of claim 11 wherein the curable liquid sealant consists essentially of an organopolysiloxane.

13. The method of claim 9 wherein the at least one feedthrough wire of the implantable medical device and the connector of the at least one conductor subassembly consist essentially of titanium or MP35N.

14. The method of claim 9 wherein:

a) the implantable medical device is comprised of a plurality of feedthrough wires extending from the control circuitry and through the wall of the housing;

b) the header assembly is comprised of a corresponding plurality of conductor subassemblies, each including a conductive connector comprising an outer surface, a distal connector end including a distal connector bore, a proximal connector end including a proximal connector bore, a central connector region that prevent communication between the distal and proximal connector bores, and a through hole extending from the outer surface into the proximal connector bore, wherein the distal end of the connector is supported by the insulative body, the proximal end of the intermediate conductor is disposed within the distal bore of the connector, and the proximal connector end including the through hole is exposed in a recess in the bottom surface of the insulative body, and wherein the proximal ends of the plurality of connectors are correspondingly positioned to receive the plurality of feedthrough wires of the implantable medical device in the proximal connector bores thereof;

c) positioning the header assembly proximate to the implantable device such that each of the plurality of feedthrough wires is disposed individually in the correspondingly positioned proximal connector bores of the plurality of connectors; and d) directing a laser beam into the through holes in the proximal connector bores and onto the individual feedthrough wires disposed therein to thereby weld the feedthrough wires of the implantable medical device to the connectors of the header assembly.

15. The method of claim 14 including providing six feedthrough wires positioned in a hexagonal pattern, and wherein there are six connectors positioned in a corresponding hexagonal pattern so that the feedthrough wires are disposable individually in the proximal bores of the connectors.

16. The method of claim 14 including providing eight feedthrough wires positioned in a pattern of two sets of four wires, and wherein there are eight connectors positioned in a corresponding pattern of two sets of four connectors so that the feedthrough wires are disposable individually in the proximal bores of the connectors.

17. The method of claim 16 wherein:

a) the implantable medical device and the header assembly each comprise a proximal side and a distal side;

b) the through holes in the proximal connector bores of a first group of connectors are viewable from the proximal side of the header assembly, and the through holes in the proximal connector bores of a second group of connectors are viewable from the distal side of the header assembly;

c) directing the laser beam into the through holes in the proximal bores of the first group of connectors from the proximal side of the header assembly, and into the through holes in the proximal bores of the second group of connectors from the distal side of the header assembly.

18. A header assembly for connecting an implantable medical device to at least one conductor lead terminating within a patient intended to be assisted by the medical device comprising a housing containing control circuitry, at least one electrical energy storage device, and at least one feedthrough wire extending from the control circuitry and through a wall of the housing, the header assembly comprising:

a) an insulative body that is mountable at a bottom surface thereof on the housing of the medical device; and b) at least one conductor subassembly comprising:

i) a terminal supported by the insulative body, wherein the terminal is directly connectable to the at least one conductor lead;

ii) an intermediate conductor comprising a distal conductor end connected to the terminal, and a proximal conductor end; and iii) a connector comprising an outer surface, a distal connector end including a distal connector bore, a solid central connector region, a proximal end including a proximal bore, and a through hole extending from the outer surface into the proximal connector bore, wherein the distal end of the connector is supported by the insulative body, the proximal end of the intermediate conductor is disposed within the distal connector bore, and the proximal connector bore is connectable to the at least one feedthrough wire of the implantable medical device.

19. The header assembly of claim 18 comprising a plurality of conductor subassemblies being connectable to a plurality of feedthrough wires extending from the control circuitry and through a wall of the housing of a medical device.

20. The header assembly of claim 19 wherein the insulative body is comprised of an extended boss supporting the distal end and the central region of each of the connectors of the plurality of conductor subassemblies.

21. The header assembly of claim 18 wherein the insulative body is of a molded polymeric.

22. The header assembly of claim 18 wherein the terminal, the intermediate conductor, and the connector of the at least one conductor subassembly consist essentially of titanium or MP35N.

23. The header assembly of claim 18 wherein the connector is of a cylindrical shape.

24. The header assembly of claim 18 wherein the medical device is selected from the group consisting of a hearing assist device, neurostimulator, cardiac pacemaker, drug pump, cardiac defibrillator, and an obesity control device.

25. The header assembly of claim 18 wherein a gap is provided in the bottom surface of the insulative body, and wherein the proximal end of the connector including the proximal bore and the through hole therein is disposed within the gap.

* * * * *